US007833542B2

(12) United States Patent
Studin

(10) Patent No.: US 7,833,542 B2
(45) Date of Patent: Nov. 16, 2010

(54) METHOD AND COMPOSITION FOR THE TREATMENT OF SCARS

(76) Inventor: Joel R. Studin, 8 Hen Hawk Rd., Great Neck, NY (US) 11024

(*) Notice: Subject to any disclaimer, the term of this patent is extended or adjusted under 35 U.S.C. 154(b) by 1148 days.

(21) Appl. No.: 10/829,316

(22) Filed: Apr. 21, 2004

(65) Prior Publication Data

US 2004/0202702 A1 Oct. 14, 2004

Related U.S. Application Data

(60) Division of application No. 10/022,216, filed on Dec. 20, 2001, now abandoned, which is a continuation-in-part of application No. 09/441,138, filed on Nov. 17, 1999, now Pat. No. 6,337,076.

(51) Int. Cl.
*A01N 25/34* (2006.01)
*A61K 8/02* (2006.01)
*A61K 31/74* (2006.01)

(52) U.S. Cl. .............. 424/402; 424/401; 424/78.03; 424/78.05; 424/78.06; 424/78.07; 514/817; 514/887

(58) Field of Classification Search ............ 424/400, 424/402
See application file for complete search history.

(56) References Cited

U.S. PATENT DOCUMENTS

| | | | | |
|---|---|---|---|---|
| 4,226,858 A | 10/1980 | Pfirrmann et al. | ............ | 424/195 |
| 4,524,065 A | 6/1985 | Pinnell | ............ | 424/94 |
| 4,560,555 A | 12/1985 | Snider | ............ | 424/78 |
| 4,645,668 A | 2/1987 | Pinnell | ............ | 424/94 |
| 4,937,078 A | 6/1990 | Mezei et al. | | |
| 5,128,375 A | 7/1992 | Tanaka et al. | ............ | 514/667 |
| 5,446,070 A * | 8/1995 | Mantelle | ............ | 514/772.6 |
| 5,534,246 A | 7/1996 | Herb et al. | ............ | 424/66 |
| 5,552,162 A * | 9/1996 | Lee | ............ | 424/646 |
| 5,578,310 A | 11/1996 | M'Timkulu et al. | ............ | 424/401 |
| 5,632,727 A * | 5/1997 | Tipton et al. | | |
| 5,639,795 A | 6/1997 | Friedman et al. | ............ | 514/772.6 |
| 5,667,773 A | 9/1997 | Farrar et al. | ............ | 424/78.05 |
| 5,702,694 A | 12/1997 | Chamness | ............ | 424/78.03 |
| 5,753,266 A | 5/1998 | Youssefyeh et al. | | |
| 5,874,074 A | 2/1999 | Smith | ............ | 424/78.02 |
| 5,885,581 A | 3/1999 | Massand | ............ | 424/195.1 |
| 5,891,076 A | 4/1999 | Fabo | ............ | 602/52 |
| 5,895,656 A | 4/1999 | Hirshowitz et al. | ............ | 424/402 |
| 5,906,814 A | 5/1999 | Epstein | ............ | 424/78.02 |
| 5,919,476 A | 7/1999 | Fischer et al. | ............ | 424/443 |
| 5,962,010 A | 10/1999 | Greff et al. | ............ | 424/443 |
| 5,968,519 A * | 10/1999 | Youssefyeh et al. | ............ | 424/755 |
| 6,325,990 B1 | 12/2001 | Laurent | ............ | 424/45 |
| 6,528,086 B2 * | 3/2003 | Zhang | | |
| 2002/0010299 A1 | 1/2002 | Guyuron et al. | ............ | 528/10 |

OTHER PUBLICATIONS

The Merck Index, an Encyclopedia of Chemicals, Drugs, and Biologicals, 12th Ed., pp. 420-421 (Edited bySusan Budavari) Merck & Co., Inc., Whitehouse Station, NJ (1996).

\* cited by examiner

*Primary Examiner*—Humera N Sheikh
(74) *Attorney, Agent, or Firm*—Frenkel & Associates, PC

(57) ABSTRACT

A method and composition for treating healed wounds including hypertrophic scars so as to prevent scarring or reduce the size and improve the appearance of scars comprises applying to the healed wound or scar a composition comprising a fluid, film-forming carrier which may contain one or more active topical ingredients, the carrier hardening to a solid, tangible, membrane juxtaposed to the skin. Novel compositions using the film-forming carrier are also useful to treat a variety of adverse skin disorders, and internal physiological conditions.

19 Claims, No Drawings

METHOD AND COMPOSITION FOR THE TREATMENT OF SCARS

RELATED PATENTS AND APPLICATIONS

This application is a division of U.S. Ser. No. 10/022,216, filed Dec. 20, 2001 now abandoned, which is a continuation-in-part of U.S. Ser. No. 09/441,138, filed Nov. 17, 1999, which is now U.S. Pat. No. 6,337,076, issued Jan. 8, 2002.

FIELD OF THE INVENTION

This invention relates to a method for the prevention or reduction of scars, as well as for improving the size and appearance of scar tissue. The invention also relates to a novel topical composition for the prevention or reduction of scar formation and for the treatment of scars and other skin conditions and diseases.

BACKGROUND OF THE INVENTION

When skin or dermis has been traumatized by cutting or burning, scar tissue is formed. In most cases, a small cut or burn area will result in a correspondingly small amount of scar tissue which is not readily discernable to a casual observer. In other cases, where the traumatized area is large and/or lengthy, scarring and scar tissue are quite apparent to a casual observer. This cannot only be embarrassing for the person who is scarred, but can be a distraction for the casual observer. The problem is compounded when, over time, scar tissue tends to darken, become thick and project outwardly from the skin surface, thus becoming more apparent.

In normal wound-healing or sore-healing processes, the abundant vascular network is regenerated in the wound or the sore during the maturing phase and the collagen fibers collect in large bundles. Changing patterns of the connective tissue matrix during growth, development, and repair during the healing of a wound and sore require a delicate balance between the synthesis and degradation of collagen. Under normal circumstances, the balance between the synthesis and degradation of collagen is maintained. However, sometimes this maturing process fails to occur, so that scar tissue remains beneath the covering epithelium for a relatively long period of time and may even develop and become enlarged. This is the clinical nature of a hypertrophic scar.

Although balanced scar formation and remodeling are essential processes in skin wound healing, disorders of excess scar formation remain a common and therapeutically refractory clinical problem. A hypertrophic scar is an excessive scar which by definition has grown in size beyond that required for normal wound healing. Hypertrophic scars can emerge from many wound types, such as from a burn or a sharp incision. A hypertrophic scar is a raised, red and itching enlargement. The scar may be tender to the touch and to other external pressure and can form on every afflicted part of the body.

Hypertrophic scars often remain for a very long time, sometimes through the entire life of the person so afflicted. A hypertrophic scar may transform to a typical soft and pale scar after a year or so. In addition to itching and being relatively unsightly, if the hypertrophic scar happens to overlay a skeletal joint, movement of the joint is often painful and restricted. In the past, such complications were overcome by covering the scar tissue with clothing, makeup, or avoiding contact with other people. This strategy is often not possible nor desirable. Scar tissue and the tissue adjacent thereto can often become hypersensitive to contact with clothing, and often, a person will not cover the scar tissue to the detriment of socialization. In some instances, a person might not be able to tolerate the application of makeup over scar tissue, again to the detriment of socialization. In other instances, a person may be required to wear a certain type or style of clothing which does not cover scar tissue locations.

Many medical care givers have recognized the problems associated with scar tissue and now include scar tissue management as part of the overall treatment of patients.

A number of techniques have been proposed for the improvement of scars. These include the application of pressure and treatments such as with corticosteroids, collagen, vitamins, such as vitamins E and A, and extracts from vegetable and animal sources. While some of these treatments have had modest success, all of the treatments can be cumbersome, inconvenient or even painful.

The use of pressure dressings is believed to be the first truly effective scar treatment. Application of pressure apparently increases the activity of collagenase, which is an enzyme capable of degrading and modeling the scar tissue and is employed by the body in the equilibrium of the formation and degradation of collagen during the healing process. However, pressure dressings are bulky rendering them uncomfortable to the user and often inconvenient to keep in place on the affected scar tissue.

The application of a steroid such as cortisone also increases the collagen degradation activity of collagenase while decreasing irritation of the scar. With a large amount of extra scar tissue such as a hypertrophic scar or keloid, depending on the severity, a physician often recommends cortisone injections. In less severe cases, cortisone creams or cortisone tapes do show modest benefit. However, creams are often inconvenient to use as they are messy and can stick to and discolor clothing. The use of tapes are also disadvantageous as such tapes often hold moisture and fall off the affected area. Further, the cortisone creams are required to be rubbed or massaged onto the scar. For some persons, this can be painful. Cortisone injections can also be very painful to the patient.

Vitamin treatment such as vitamin E is believed to decrease the expression of collagen forming genes during the wound healing process and also may soften scars. Cutting vitamin E gelatin capsules in half and squeezing out the oil has been the most common way to apply vitamin E to wounds. Obviously, a vitamin E oil is messy and cutting the capsules in half is a tedious process. The addition of vitamins A and B in creams and lotions is also known, but such creams and lotions are often oily to the touch and do not dry so as to remain in an oily condition or take a long period of time to rub completely into the skin. Again, rubbing or massaging a cream or oil into and/or onto certain scar tissue can be painful to some persons.

It has been discovered in recent years that the shrinkage of hypertrophic scars can be increased by applying silicone-gel plates or sheets to the scars. The exact mechanism by which the silicone-gel interacts with such scars has not been established, however. A number of products are available commercially for this purpose, for instance such products as Dow Corning Silastic Sheeting, Cica-Care (Smith & Nephew), Epi-Derm (Biodermis), Nagosil (Nagor), among others. These products have the form of molded silicone-gel sheets having a thickness of 2-4 millimeters. In treating hypertrophic scars, these sheets are placed over the scars and are worn for a relatively long period of time, often from 3-12 months, until the scars either have decreased or have regenerated. Examples of recent patents which disclose such silicone-gel sheets include U.S. Pat. Nos. 5,759,560; 5,891,076; 5,895,656; and 5,919,476.

The known silicone sheets are relatively rigid and after having been placed over the scar have insufficient adhesion to remain securely in position without some form of assistance. Consequently, it is necessary to secure the sheets against the skin with the aid of securing, stocking, bandage, self-adhesive tape or some like means. The sheets can often trap too much moisture causing irritation on the affected area. Additionally, gel sheets of the type that utilize silicone are tacky to the touch, both on the inner body, body contacting surface and the exterior surface. Having a body contacting surface which is tacky to the touch is advantageous and desirable. However, having an exterior which is tacky to the touch is not. A disadvantage of having a tacky exterior is that articles of clothing tend to adhere to the gel sheet. This presents several problems. One problem is that often the gel sheet adheres to an article of clothing with greater force than it adheres to the skin. Thus, when the article of clothing is removed, the gel sheet is removed from the body. Another problem is that the articles of clothing would adhere to the gel sheet and prevent normal range of motion. An additional problem encountered with gel sheets which are tacky to the touch is that they tend to become soiled more quickly.

Similar silicone materials in the form of topical gels, cremes, and ointments are also available on the market for treatment of wounds, e.g. Kelocote.® Again, these materials remain greasy or oily on the skin and have the disadvantages as described above with respect to comfort and soiled clothing.

Other physical treatments are available, including surgery, X-ray therapy and cryotherapy. Such treatments are expensive or potentially dangerous and not normally recommended.

Accordingly, while there have been physical treatments, compositions and/or articles which contain medicaments which have had modest success in reducing, softening and lightening hypertrophic scars, these prior attempts are expensive, inconvenient to use, difficult to apply or simply have not been very effective in achieving the desired purpose.

SUMMARY OF THE INVENTION

As expressed above, existing therapy for hypertrophic scars and keloids has included surgery, mechanical pressure, X-ray irritation, cryotherapy, and the application of various medicaments such as steroids, vitamins, as well as vegetable and animal extracts. Again, there are many disadvantages associated with each of these methods. Thus, surgical removal of the scar tissue is often incomplete and can result in the development of hypertrophic scars and keloids at the incision and suture points. X-ray therapy is the only predictably effective treatment to date, however, because of its potential for causing cancer, X-ray therapy is not generally recommended or accepted. The most common approach to control hypertrophic scar and keloid formation is to apply pressure, which appears to be effective in many instances. However, this treatment has limited application, generally based on the size and location of the scar tissue on the body. Steroid injections are unpredictable and often result in depigmentation of the skin. Application of silicon-based gels such as in sheets has resulted in general improvement in the appearance and size of treated scars, but the mechanism of such healing is not known and the inconvenience of such silicone-gel sheets has been discussed previously.

Accordingly, a primary objective of the present invention is to provide an effective and, yet convenient to use composition which can prevent or reduce scarring of healed wounds or improve the size and appearance of formed scars, in particular, hypertrophic scars.

One aspect of the present invention is directed to a method for the treatment of healed wounds or hypertrophic scars with a medicament capable of preventing scarring or reducing the size or improving the appearance of scars. The medicament is mixed within a film-forming carrier which can be accurately and directly applied as a fluid to the affected area, including scar tissue, and which results in the formation of a tangible membrane juxtaposed to the affected skin to hold the medicament in place. This tangible membrane differentiates from the coating residue remaining after application of prior art ointments, gels, cremes, liquids or sprays. Such residues do not form a removable physical lamina as in the present invention. A number of film-forming carriers are known which dry in place and are not greasy or oily to the touch after application and drying as has characterized carriers previously used with the application of vitamins or other vegetable or animal extracts or with steroids. The film-forming carrier can be applied directly onto the healed wound or formed scar to be treated without the need for rubbing or the application of pressure such as with oily or greasy carriers which application can often be painful to the person whose wound or scar is being treated.

In another aspect of the present invention, a composition is provided which is effective for reducing the size and appearance of scars and can be readily and accurately applied directly to a healed wound or to a scar, such as a hypertrophic scar without the problems associated with oils and greases, or wraps and sheets, which have been used to merely apply pressure or provide contact with silicone-gels. In this aspect of the invention, a composition is provided comprising a fluid, film-forming carrier which includes a dermatologically effective steroid such as a corticosteroid which can be applied directly onto the healed wound or the scar tissue and which carrier forms a tangible membrane juxtaposed to the affected tissue and which contains the steroid medicament.

In an alternative to the invention described immediately above, a steroid, silicone-gel or vitamin E, or mixtures thereof are provided in a fluid, film-forming carrier as above described and which can be used to treat not only wounds or scars but a variety of skin conditions and disorders.

Another aspect of this invention is the use of a fluid, film-forming carrier which forms a tangible membrane juxtaposed to the skin to administer medicaments such as chemotherapeutic (anti-cancer) agents, analgesics, and other physiological-affecting agents topically or parenterally.

In still another aspect of the present invention, a composition for the treatment of healed wounds or hypertrophic scars so as to prevent scarring or reduce the size of the scar or improve the appearance thereof is provided by combining a dermatologically effective steroid such as, hydrocortisone, a silicone-gel and, optionally, vitamin E in a single fluid carrier which can be applied directly to the wound or scar tissue and presents for the first time a multicomponent medicament composition combining the effective properties of components which have been used singly. It has been found that the steroid, silicone-gel and vitamin E can be effectively mixed within a fluid film-forming carrier and be applied directly to the wound or scar tissue in a convenient manner. The composition hardens to a tangible membrane remaining juxtaposed to the affected area without the need for wraps, tapes, and without the disadvantages of oils or greases which can discolor clothing and need to be rubbed or massaged onto and into the scar.

In yet another aspect of this invention, it has been found that the application of a film-forming composition as a fluid onto healed wounds or scars, and drying the composition to a tangible film juxtaposed on the affected area, even without a medication therein, can be effective to reduce scarring due to the pressure which is applied onto wound or scar tissue when the solid film forms.

In still yet another aspect of this invention, a healed wound or scar is treated by the topical application of collagenase onto the affected area. The collagenase can be incorporated into the fluid, film-forming carriers of this invention or any known topical or transdermal carrier, including ointment, cremes, gels and patches.

DETAILED DESCRIPTION OF THE INVENTION

The method of the present invention is directed to the application of a medicament contained in a fluid, film-forming carrier to the affected wound or scar tissue. As described herein, the film-forming carrier refers to a fluid film which results upon application to the skin in the formation of a tangible membrane juxtaposed to the skin surface. The film-forming carrier contains one or more medicaments (active ingredients) which applied onto a healed wound or scar tissue and held in place by the carrier film can prevent or reduce scar formation or can reduce the size of a hypertrophic scar and/or improve the appearance thereof. Thus, the method of the present invention is the application of a fluid, film-former and one or more effective scar-treating medicaments to a healed wound or hypertrophic scar. The film-former forms a protective membrane over the site of application to maintain contact of the active ingredients with the wound or scar and prevents removal of the active ingredients from the site. In its broadest aspect, the film forming carrier alone can provide effective scar treatment since when the carrier forms the tangible film, pressure is applied to the affect area. The application of pressure is known to reduce scarring by increasing the activity of collagenase as described previously. Thus the application of the carrier alone as a fluid without the need for massaging or rubbing the fluid onto the wound or scar and the drying or curing of the carrier into a solid film as previously described provides a convenient, useful and effective scar prevention or scar reduction treatment.

The method of this invention is directed to treatment of wounds such as formed as the result of accidental skin trauma, e.g. cuts, bruises, burns, or due to surgical procedures. The wounds to be treated should be healed, i.e. reepithelized such that the exterior dermis layer of the wound is intact. For example, a surgical wound can be treated immediately after surgical stitching has been removed, or an accidental wound can be treated after it has reepithelized. Wounds can be treated hours to several months after the trauma depending on the extent of the wound and the vascularity of the area wounded. It is believed the method of this invention can prevent the formation of scarring by maintaining the proper balance of collagen synthesis and degradation immediately after reepithelization of the wound. In any event, scarring can be reduced by application to the healed wound of the medicament in the film-forming carrier. The method of this invention is also directed to treatment of scars which have already formed, such as hypertrophic scars. Reduction of hypertrophic scars and improvement in coloration and other appearance has been found with the method of this invention.

The film-formers which are preferably used in the method of the present invention are cellulosic derivatives such as methyl cellulose which can form films from aqueous solutions and nitrocellulose which can be used in organic solvents. Collodion or Flexible Collodion are very useful fluid, film-formers which can be used. Collodion is a solution of 4 grams of pyroxylin (chiefly nitrocellulose) in 100 ml. of a mixture of 25 milliliters alcohol and 75 milliliters ether. Collodion is a colorless or slightly yellow, clear or slightly opalescent syrupy liquid. The flexible Collodion comprises simple Collodion with the addition of camphor and 3% castor oil (by weight). Flexible Collodion is slightly yellow and is a syrupy liquid which contains 67% either and about 22% absolute alcohol by volume. When the Collodion or Flexible Collodion evaporates it leaves a tough and colorless solid, tangible film, not merely a coating residue as do previous carriers such as ointments, cremes, gels, and the like. Polyvinylalcohol is also a useful aqueous, film-forming carrier which can be used in this invention. More generally, any film-forming carrier which can be applied to the affected area as a fluid regardless of viscosity and dries or otherwise cures to a solid, non-greasy or non-oily, tangible membrane film can be used alone or with other medicaments to prevent or reduce scarring. Silicone resins which are fluid but cure to solid films in air such as those having the consistency of caulking, as well as other polymers are useful in this invention. The topical compositions of the invention may also contain a solvent added to the carrier which serves to reduce carrier viscosity and/or dissolve the active ingredient. Examples of solvents which may be used include water and organic solvents such as acetone, alcoholic or ethers.

In the preferred method of this invention, an active ingredient which is effective to prevent or reduce scar formation or to treat hypertrophic scars is included in the film-forming carrier. Any active ingredient which is so effective, known or unknown at the present time, is useful in the method of this invention. Such active ingredients include dermatologically active steroids, e.g. corticosteroids, vitamins and other vegetable and animal extracts known to treat scars, as well as silicones, including silicone-gels which have been used in silicone-gel sheets and plates.

Another active which can be used is the enzyme collagenase. Enzymes are proteinaceous substances which act as catalysts for biological reactions; in some cases hydrolysis reactions and in others oxidation-reduction processes. Some enzymes have broad activity and others, such as collagenase (Clostridiopeptidase A) produced from the bacterium clostridium hystolyticum, have very specific activity. Highly purified collagenase has been prepared and been found uniquely capable of cleaving bonds in the collagen structure permitting other enzymes to act on the resulting molecular fragments. Purified collagenase has been demonstrated to be relatively safe even in large doses (thousands of units) in animals and in contact with human blood vessels, nerves and bones.

In preparing topical compositions for use in the method of this invention, there can be added conventional adjuvants such as propionic acid, propylene glycol, acetone and lactic acid, conventional penetration enhancers such as erucic acid, oleic acid and bahemic acid; conventional buffers, preservatives, hydrophilic emulsifiers, lipophilic emulsifiers, sunscreening agents, perfumes, emollients, deodorants, humectants, and the like. Colorants may also optionally be added in the useful compositions of the invention. Current Collodion-based FDA monograph approved formulas may be employed in such topical liquid compositions.

Preferably, in the method of this invention, the composition is applied to a healed wound or to the scar tissue to be treated by any common applicator such as a brush, roll, squeeze tube, sprayer or eye dropping apparatus conveniently used to apply compositions to the skin. The compositions may also be applied by impregnating a porous base with the composition and wiping the composition onto the affected area or where the porous base includes an adhesive, securing the porous base to the skin adjacent to the wound or scar and wherein the film-former and active ingredient are placed on the area to be treated. The composition used in the method of the present invention can be a relatively low or high viscous liquid which can be applied directly and accurately onto the wound or scar tissue and does not require the application of additional pressure or rubbing as do certain oils and greases which have been previously utilized. Accordingly, it is believed that the use of a film-former, which forms a tangible, solid film with optionally one or more medicaments to treat healed wounds or hypertrophic scars is novel.

In another aspect of the present invention, a composition is provided to treat wounds or hypertrophic scars so as to prevent scar formation or reduce the size of the scars and improve the appearance thereof. In this aspect of the invention, an active ingredient in the form of a steroid is added to the film-forming carrier. Thus, it has been found that dermatologically active steroids which an be applied topically, such as hydrocortisone, betamethasone, diflusinol and any other known corticosteroids and the like, as well as pharmaceutically acceptable salts thereof including chloride, acetate, etc., can be added to the film-forming carrier in amounts of from about 0.01% to about 70% by weight to yield a composition which can be readily and directly applied to the affected tissue. The composition forms a solid, tangible film as above described which maintains the steroid active ingredient juxtaposed to the wound or scar tissue and provides an advantageous and continuous healing effect of the steroid. As previously disclosed, adjuvants typically used for topical compositions can be added, including solvents, penetration enhancers, emollients, buffers, etc. as long as such addition does not adversely interfere with the effectiveness of the steroid.

The present invention provides a further composition which is useful to prevent scarring or to improve the size and appearance of hypertrophic scars. The composition again is based upon the film-forming carrier. In this aspect of the invention, two or more medicaments which are active to improve hypertrophic scars and which have been used on a individual basis are now combined in the film-forming carrier which forms a solid film on the affected area and provides a base from which the actives can act upon the healed wound or the scar tissue and provide the desired improvement. Thus, in accordance with this invention, the carrier has incorporated therein at least one dermatologically active steroid, a silicone-gel and, optionally, vitamin E.

The dermatologically active steroid which can be used is that described above, in particular, corticosteroids such as hydrocortisone, betamethasone, diflusinol and the like, including pharmaceutically acceptable salts thereof.

Additionally, it has been found that the carrier can still remain film-forming and a particularly advantageous composition can be formed by the addition of silicone to the composition either alone or in addition to the dermatologically active steroid. The silicones which can be added to the composition of this invention are those which have been found effective to improve the appearance and size of hypertrophic scars. Silicones are a group of completely synthetic polymers containing the recurring group —$SiR_2O$— wherein R is a radical such as an alkyl, phenyl, or vinyl group which may be substituted or unsubstituted. The simpler silicones are oils of very low melting point, while at the other end of the scale of physical properties are highly cross-linked silicones which form rigid solids. Intermediate physical properties are silicone elastomers such as gels and rubbers. A variety of silicone-gels have been used as wound dressings as disclosed in U.S. Pat. No. 4,838,253 assigned to Johnson and Johnson and U.S. Pat. No. 4,991,574 assigned to Dow. An example of a useful silicone-gel which has been used is marketed under the tradename SILASTIC®.

While it has not been proven conclusively as to how the silicone-gels act on the scar tissue to improve them, based n experiments involving the measurement of physical parameters associated with the use of such gels, investigators have concluded that the mode of operation of the silicone-gel and scar treatment did not involve pressure, temperature, oxygen, tension or occlusion. Rather, as reported, the likely mechanisms involved both hydration of the stratum corneum and the release of a low molecular weight silicone fluid from the gel.

Any of the known silicone-gels which have been previously used for wound dressings as described above can be used as additives in the composition of this invention. In general, the silicone-gel will have a viscosity at 25° C. of about 25-30,000 cps, preferably 100-30,000 cps. A phenyl trimethicone such as Dow Corning 556 fluid or a non-volatile polydimethylsiloxane are examples of silicone fluids which can be used.

Although optional, it is preferred to include any one or more forms of vitamin E to the composition. In this most preferred embodiment, three active ingredients which have been known to treat hypertrophic scars on an individual basis have been found to be extremely useful in combined form in a single film-forming carrier without disadvantageous interactions between the components. Useful compositions can comprise from about 0.01-70% by weight of the steroid, preferably from about 0.05-10% of the steroid; 0.01-70%, preferably 5-25% silicone and 0-25%, preferably 0.1 to 25% vitamin E. The balance is the film-forming carrier, such as listed previously.

Compositions of this invention have been found useful when applied once or twice daily for 3-4 months to yield the best results of softening, shrinking and lightening hypertrophic scars. Less dosing to prevent healed wounds from scarring may be needed.

As previously stated, other adjuvants can be added to enhance penetration of the active ingredients, control moisture levels on the scar tissue, provide preservative and antibacterial effects, etc. In another preferred embodiment, small amounts of xanthan gum can be added which provides both thickening qualities and acts as a dispersion enhancer for the active ingredients, including the steroids such as hydrocortisone and the silicone component. If xanthan gum is added, it should be present in amounts of from about 0.5-4%, preferably from about 0.75-2.5% by weight.

The invention is still further directed to a topical composition which can be used to readily and effectively treat a variety of adverse skin conditions, including hypertrophic scars, eczema, psoriasis, atopic dermatitis, insect bites, poison ivy and like plant toxins, and other infectious and immunological skin disorders. In this aspect of the invention, topical actives such as steroids, including corticosteroids, silicone-gels, i.e. non-volatile polysiloxanes, vitamins, including vitamins A and E, or mixtures thereof, are incorporated into the film-forming carrier of this invention and which forms a non-sticky or non-greasy tangible film on the skin surface. The levels of each active component will vary depending on the skin disorder being treated and can be readily determined from known usages of the actives which have been contained in other carriers such as lotions, greases, oil or porous structures, e.g. bandages, gauze, etc. In general, levels of 0.01 wt. % to 75 wt. % are most practical but, variations are acceptable within the scope of this invention.

The film-forming carriers of the present invention may also be used to topically and parenterally deliver medications which have been previously applied by injection or transdermally such as by physical patches or even orally. Thus, film-forming carriers of this invention can contain such medicaments such as chemotherapeutic agents which can be applied to the skin to topically treat skin cancers or form a reservoir which when applied to the skin can transdermally direct the medicament to the underlying tissue and the blood stream. Likewise, analgesics such as topical anesthetics as well as parenteral and orally active analgesics can be transdermally administered utilizing the film-forming carrier of this invention. Still further, vasodilators, bronchial dilators, antihistamines, such as benadryl or the like, addictive suppression agents or other therapies such as nicotine can be topically applied for transdermal application using the film-forming carriers of this invention. Any other medicament which has an internal physiological affect and can be otherwise transdermally administered can be incorporated in the fluid, film-forming carriers of this invention and conveniently administered to the patient by simply applying the composition to the skin. The film-forming carrier containing the therapeutic agent dries or otherwise cures to a tangible membrane which holds the medicament in contact with the skin. Levels of active in the fluid, film-forming carrier of this invention will obviously vary depending on the type of agent and can be determined by those skilled in the art. The fluid carriers of this invention allow for rapid and easy application of the active, such as by any known fluid applicator. Moreover, the active can be administered by a single application or reapplied subsequent to hardening of the carrier with or without removal of the underlying film.

The compositions of the present invention are believed to be novel. Film-forming materials alone or containing a steroid and/or silicone have not been used to treat healed wounds or hypertrophic scars. While hydrocortisone is available as a topical ointment or cream and silicone is available as a liquid, an ointment or as a bandage sheet that must be cut and adhered to the skin with tape or other mechanism, the composition of the present invention can combine one or both of these active agents or include any of the topically active or internal physiologically active therapeutic agents discussed previously and dispense such agents into a matrix of an occlusive dressing that when brushed or otherwise applied onto the skin as a fluid, dries or otherwise cures quickly to solid form, keeps the active ingredients in contact with the skin to exert their intended action, and may be peeled off, either at completion of therapy or to apply subsequent doses. The compositions of this invention require no mechanical aid, i.e. adhesive bandage, gauze or impregnated sheet coverings. Application is simply accomplished by directing the fluid base, preferably medicated, onto the affected area and allowing to harden. The liquid base fully hardens, creating a solid, flexible occlusive bandage covering. While the compositions can be easily brushed on, other applicators can be used including a dispensing-type device which will roll the material onto the affected area, extrude the composition such as from a tube, as well as apply from spray-type devices or eye dropper-type mechanisms for less viscous composition. What is important is that the carrier of this invention does not need to be rubbed or massaged onto the affected area which can be painful in certain circumstances. Further, the carrier hardens to a solid film which will not stick to clothing.

EXAMPLE 1

The following composition was prepared as a scar-healing composition. The composition was prepared by adding the ingredients shown to the carrier base, which in this instance was Flexible Collodion, USP.
10 wt. % silicone 556
1 wt. % hydrocortisone hydrochloride
0.5% alpha-tocopherol (vitamin E)
1.2 wt. % xanthan gum
balance of Flexible Collodion, USP

EXAMPLE 2

An alternative formulation was prepared that did not include the xanthan gum.
12 wt. % silicone 556
0.5 wt. % hydrocortisone hydrochloride
0.5 wt. % vitamin E
balance Flexible Collodion, LTSP

EXAMPLE 3

The following composition is useful for applying a topical anesthetic.
98 wt. % Flexible Collodion
2 wt. % Lidocaine The Examples are not intended to strictly limit the invention to the embodiments shown. It should be understood that the foregoing detailed description is given merely by way of illustration. Obviously, many modifications and variations of the invention as hereinbefore set forth can be made without departing from the spirit and scope thereof, and therefore, only such limitations should be imposed as are indicated by the appended claims.

I claim:

1. A method of treating healed wounds so as to reduce scarring and/or improve the appearance of scars comprises; applying onto a healed wound a composition comprising a fluid, film-forming carrier, and subsequently hardening the carrier into a tangible membrane juxtaposed to the healed wound thereby reducing scarring or improving the appearance thereof.

2. The method of claim 1, wherein the film-forming carrier comprises Collodion or Flexible Collodion.

3. The method of claim 1, wherein said composition is applied onto the healed wound by brushing, rolling, extruding or applying drops of said composition.

4. The method of claim 3, wherein said composition is applied to the healed wound by brushing.

5. The method of claim 1, wherein said composition includes an active ingredient capable of reducing scarring or improving the appearance of scars selected from a topical steroid, silicone-gel, vitamin and mixtures thereof.

6. The method of claim 5, wherein said active ingredient includes a corticosteroid or a pharmaceutically acceptable salt thereof.

7. The method of claim 5, wherein said active ingredient comprises a combination of a topical steroid and silicone-gel.

8. The method of claim 5, wherein said active ingredient is a silicone-gel.

9. The method of claim 7, wherein said composition further includes vitamin E.

10. The method of claim 1, wherein said film-forming carrier is a cellulosic derivative.

11. The method of claim 10, wherein said cellulosic derivative is nitrocellulose.

12. The method of claim 10, wherein said cellulosic derivative is methyl cellulose.

13. The method of claim 1, wherein said film-forming carrier comprises a silicone resin.

14. The method of claim 1, wherein said healed wound comprises a hypertrophic scar.

15. The method of claim 1, wherein said healed wound is one formed after surgery.

16. The method of claim 1, wherein said healed wound is formed after accidental trauma.

17. A method of treating healed wounds so as to reduce scarring and/or improve the appearance of scars comprises: applying onto a healed wound a topical composition comprising collagenase.

18. The method of claim 17, wherein said topical composition comprises collagenase contained within a fluid, film-forming carrier, subsequent to applying said composition onto said healed wound, hardening said carrier into a tangible membrane juxtaposed to the healed wound.

19. The method of claim 17, wherein said topical composition comprises collagenase contained within a topical creme, ointment, lotion or gel.

* * * * *